United States Patent [19]

Galantay

[11] 4,032,580
[45] June 28, 1977

[54] ANTI-INFLAMMATORY 1-PHENYL-2,3-BUTADIEN-1-OLS, METHODS OF USE AND COMPOSITIONS CONTAINING SAME

[75] Inventor: Eugene E. Galantay, Liestal, Switzerland

[73] Assignee: Sandoz, Inc., E. Hanover, N.J.

[22] Filed: Sept. 18, 1975

[21] Appl. No.: 614,538

Related U.S. Application Data

[60] Division of Ser. No. 405,478, Oct. 11, 1973, Pat. No. 3,929,902, which is a continuation-in-part of Ser. No. 219,129, Jan. 19, 1972, abandoned.

[52] U.S. Cl. .................. 260/618 D; 260/247.7 Z; 260/268 PH; 260/618 R; 424/250; 424/343; 424/248.57; 424/248.58
[51] Int. Cl.² ........................................ C07C 33/06
[58] Field of Search ............... 260/618 R, 618 D; 424/343

[56] References Cited

UNITED STATES PATENTS

| 2,930,817 | 3/1960 | Fert et al. ............... 260/618 R |
| 3,435,075 | 3/1969 | Glamkowski et al. ......... 260/618 R |
| 3,629,314 | 12/1971 | Kulka ..................... 260/618 R |
| 3,723,091 | 3/1973 | Allais et al. ............. 260/618 R |
| 3,806,551 | 4/1974 | Blume .................... 260/618 R |
| 3,888,933 | 6/1975 | Anderson ................. 260/618 R |
| 3,891,716 | 6/1975 | Anderson ................. 260/618 R |

OTHER PUBLICATIONS

Bardone–Gaudemar, "Comp. Rend. (Pans)," Tome 245, pp. 324–326, (1957).
Bertrand et al., "Comp. Rend. (Pans)," Tome 255, pp. 1305–1307, (1952).

*Primary Examiner*—Norman Morgenstern
*Attorney, Agent, or Firm*—Gerald D. Sharkin; Richard E. Vila; Frederick H. Weinfeldt

[57] ABSTRACT

Disclosed are compounds of the class 1-phenyl-2,3-butadien-1-ol e.g. 2-(p-biphenyl)-3,4-pentadien-2-ol, which are useful by reason of their pharmacological activity in animals, e.g., as anti-inflammatory agents and tranquilizers. Said compounds can be prepared, e.g., by reduction of a corresponding 4-substituted-1-phenyl-2-butyne-1-ol with a complex hydride such as lithium aluminum hydride.

19 Claims, No Drawings

ANTI-INFLAMMATORY 1-PHENYL-2,3-BUTADIEN-1-OLS, METHODS OF USE AND COMPOSITIONS CONTAINING SAME

This is a division of copending application Ser. No. 407,478, filed Oct. 11, 1973 (now U.S. Pat. No. 3,929,902), which is a continuation-in-part of then copending application Ser. No. 219,129, filed Jan. 19, 1972 (now abandoned).

The invention relates to 1-phenyl-2,3-butadien-1-ols and to pharmaceutical compositions and method utilizing the pharmacological activity of said compounds, as well as to intermediates therefor.

The compounds of the present invention can be represented by the formula I

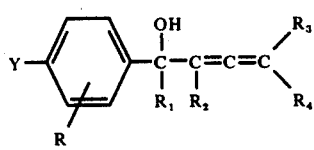

wherein
R is a hydrogen atom or halo having an atomic weight of from about 19 to 80, i.e., fluoro, chloro or bromo;
$R_1$ is a hydrogen atom or alkyl of 1 to 3 carbon atoms,
$R_2$ is a hydrogen atom or methyl, and
$R_3$ and $R_4$ are, independently, a hydrogen atom or alkyl of 1 to 3 carbon atoms provided that at least one of $R_3$ and $R_4$ is a hydrogen atom when $R_2$ is methyl, and
Y is halo having an atomic weight of from about 80 to 127, i.e., bromo or iodo, isobutyl, tert.butyl, cyclohexyl, cyclohexenyl, e.g., cyclohex-1-enyl, or substituted or unsubstituted phenyl of the formula

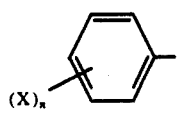

wherein
X is a hydrogen atom, halo having an atomic weight of from about 19 to 80, i.e., fluoro, chloro or bromo, or lower alkoxy, e.g., having from 1 to 4 carbon atoms, such as methoxy, ethoxy, propoxy, or butoxy, including isomeric forms where such exist; and
n is an integer from 1 to 5, preferably n is 1 or 2; or
Y is a radical of the formula

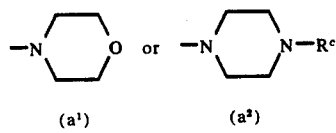

wherein $R^c$ is a hydrogen atom or alkyl having 1 to 3 carbon atoms.

With reference to $R^1$, $R^3$, $R^4$, and $R^c$, defined above; when any of them represents an alkyl group having from 1 to 3 carbon atoms, such substituent is methyl, ethyl, n-propyl or isopropyl.

The compounds of formula I in which $R_2$ is hydrogen, i.e., the compounds of formula Ia

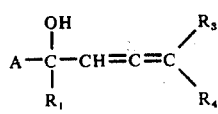

wherein
$R_1$, $R_3$ and $R_4$ are as defined above; and
A is the moiety

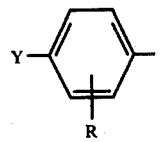

wherein R and Y are as defined above, can be prepared by subjecting a compound of formula II

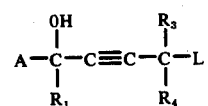

wherein
A, $R_1$, $R_3$ and $R_4$ are as defined above and
L is

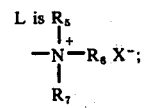

tetrahydrofuran-2-yloxy; tetrahydropyran-2-yloxy or 4-methoxy-tetrahydropyran-4-yloxy; halo, e.g., fluoro, chloro, bromo or iodo; alkylsulfonyloxy in which the alkyl group may be substituted, e.g. halo, or unsubstituted and contain from 1 to as many as 16 or more, preferably 1 to 6, carbon atoms, e.g. methane sulfonyloxy, ethanesulfonyloxy, 3-chloropropanesulfonyloxy, 1-hexadecanesulfonyloxy or arylsulfonyloxy in which the aryl group is phenyl, naphthyl or mono or polysubstituted phenyl in which the substituents are, e.g. alkyl of 1 to 6 carbon atoms, alkoxy of 1 to 6 carbon atoms, halo, or nitro;

$R_7$ represents alkyl having 1 to 4 carbon atoms, e.g. methyl, ethyl, propyl or butyl including isomeric forms where they exist, although the unbranched alkyls are preferred, especially methyl, and $R_5$ and $R_6$ independently represent alkyl having 1 to 4 carbon atoms; cycloalkyl having 5 or 6 ring carbons, i.e. cyclopentyl or cyclohexyl; or together, with N, represents a heterocyclic ring having 5 to 7 members selected from the group consisting of pyrrolidino, piperidino, homopiperidino, morpholino, thiomorpholino, and their alkyl substituted derivatives containing 1 to 3 alkyl groups of 1 to 4 carbon atoms;

X is an anion derived from a mineral acid or an organic sulfonic acid, provided that X is not fluoro, to the action of a complex hydride reducing agent of the formula IIIa or IIIb:

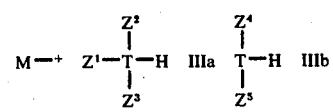

wherein
T is a "tervalent" transition metal or non-metal such as aluminum, gallium or boron, i.e. an element of Group IIIa of the periodic table having atomic weight of from 10 to 70; and $Z^1$, $Z^2$ and $Z^3$ are, independently, a hydrogen atom, alkyl of 1 to 6 carbon atoms, alkoxy of 1 to 6 carbon atoms; or alkoxyalkoxy having from 2 to 6 total carbon atoms;

$Z^4$ and $Z^5$ are, independently, hydrogen or alkyl of 1 to 6 carbon atoms; and M is an alkali or alkaline earth metal, such as lithium, sodium, potassium, calcium or magnesium,
such as lithium aluminum hydride, sodium dihydrobis (2-methoxyethoxy) aluminate, sodium diethyl aluminum dihydride, lithium borohydride, lithium gallium hydride, magnesium aluminum hydride, lithium diisobutylmethyl aluminum hydride, lithium trimethoxy aluminum hydride, diethyl aluminum hydride and diborane, preferably lithium aluminum hydride or sodium dihydrobis (2-methoxyethoxy) aluminate.

The compounds of formula I in which $R_2$ is methyl, i.e. the compounds of formula Ib $$A-\underset{\underset{R_1}{|}}{\overset{\overset{OH}{|}}{C}}-\underset{\underset{CH_3}{|}}{C}=C=CH-R_8 \qquad Ib$$

wherein

A and $R_1$ are as defined above, and $R_8$ is the same as either $R_3$ or $R_4$ defined above, can be prepared by treating a compound of the formula IV $$A-\underset{\underset{R_1}{|}}{\overset{\overset{O-G}{|}}{C}}-\underset{\underset{CH_3}{|}}{C}=C=CH-R_8 \qquad IV$$

wherein A, $R_1$, $R_8$ are as defined above, and

G is a protecting group stable under basic conditions, e.g. tetrahydropyran-2-yl tetrahydrofuran-2-yl and the like
with a mild acid, e.g. paratoluene sulfonic acid.

The process for preparing the compounds of formula Ia should be carried out in a medium which is not detrimental to the reaction, such as in an aprotic organic solvent, e.g. an ether such as diethyl ether, tetrahydrofuran or dioxane, an aromatic medium, such as benzene, toluene or pyridine or a saturated aliphatic hydrocarbon, such as pentane, hexane or octane. The use of a solvent which is capable of dissolving the compound II, at the reaction temperature is preferred. The medium may be a mixture or a single material.

The reaction, e.g. may be carried out at from about $-40°$ to $+120°$ C., e.g. at the boiling point of the medium. However, temperatures of from about $-10°$ to $+50°$ C. are preferred. While the higher temperatures result in a faster reaction rate, reactions carried out at lower temperature tend to give purer products. The reaction product (compound Ia) may be recovered by conventional means, e.g. by carefully adding a small amount of water or aqueous sodium sulfate to the reaction mixture, filtering off the inorganic by-products or hydrolysis products of the hydride ion source, and then separating the Compound Ia from the organic phase by such means as precipitation, extraction, crystallization, chromatography or liquid-liquid extraction. As will be appreciated by those skilled in the art, it is preferred to exclude moisture from the reaction, e.g. by use of anhydrous solvents and conditions. The reaction may be advantageously carried out in an inert atmosphere, e.g. under nitrogen gas.

The process for producing compounds of formula Ib, which comprises the splitting off of the protecting group G is effected under the acid condition usually employed for such a hydrolysis reaction, e.g. by using toluene acid hydrate in methanol, ethanol or benzene. The protecting group G of compound IV is preferably a tetrahydropyranyl group.

The compounds of formula II in which L is a quaternary ammonium radical, i.e. the compounds of formula IIa $$A-\underset{\underset{R_1}{|}}{\overset{\overset{OH}{|}}{C}}-C\equiv C-\underset{\underset{R_4}{|}}{\overset{\overset{R_3}{|}}{C}}-L' \qquad IIa$$

wherein

A, $R_1$, $R_3$ and $R_4$ are as defined above and $$L' \text{ is } -\underset{\underset{R_7}{|}}{\overset{\overset{R_5}{|}}{N}}{}^+-R_6 \; X^-$$

in which $R_5$, $R_6$, $R_7$ and X are as defined above, can be prepared by quaternizing a compound of the formula V $$A-\underset{\underset{R_1}{|}}{\overset{\overset{OH}{|}}{C}}-C\equiv C-\underset{\underset{R_4}{|}}{\overset{\overset{R_3}{|}}{C}}-N\underset{\diagdown R_6}{\diagup R_5} \qquad V$$

wherein A, $R_1$, $R_3$, $R_4$, $R_5$ and $R_6$ are as defined above, with a compound of the formula VI $$R_7 X \qquad VI$$

wherein $R_7$ and X are as defined above.

The quaternization can be carried out in the conventional manner, e.g. in a suitable solvent such as acetone, at a temperature of from $-20°$ to $+30°$ C., neither the solvent nor the temperature being critical. A preferred compound VI is methyl iodide.

The compounds of formula II in which L is tetrahydrofuran-2-yloxy, tetrahydropyran-2-yloxy or 4-methoxy-tetrahydropyran-4-yloxy, i.e. the compounds of formula IIb $$A-\underset{\underset{R_1}{|}}{\overset{\overset{OH}{|}}{C}}-C\equiv C-\underset{\underset{R_4}{|}}{\overset{\overset{R_3}{|}}{C}}-L'' \qquad IIb$$

wherein

A, $R_1$, $R_3$ and $R_4$ are as defined above and

L'' is tetrahydrofuran-2-yloxy, tetrahydropyran-2-yloxy or 4-methoxy=tetrahydropyran-4-yloxy
can be prepared by reacting a compound of the formula VII $$A-\underset{\underset{R_1}{|}}{C}=O \qquad VII$$

wherein A and $R_1$ are as defined above, with Grignard reagent formed by treating a compound of the formula VIII

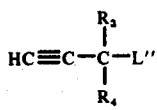   VIII wherein $R_3$, $R_4$ and $L''$ are as defined above, with ethyl magnesium bromide.

The compounds of formula II in which L is halo other than iodo, i.e., those compounds of formula IIc

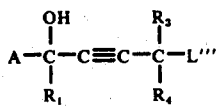   IIc wherein
A, $R_1$, $R_3$ and $R_4$ are as defined above and
$L'''$ is fluoro, chloro or bromo
can be prepared by reacting a compound of the formula IX

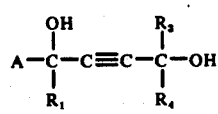   IX wherein A, $R_1$, $R_3$ and $R_4$ are as defined above with the appropriate halide selected from the group of thionyl chloride or bromide, phosphorus pentachloride or bromide and hydrocarbon sulfonyl fluorides, e.g. benzyl sulfonyl fluoride, tosyl fluoride and mesyl fluoride in an organic medium such as hexane, benzene or dimethoxyglycol. For the chlorination and bromination a tertiary amine base, such as pyridine, is included in the reaction mixture and the reaction temperature is about 0° to 20° C. For the fluorination the reaction temperature is 0° to about 150° C.

Compounds of formula II in which L is iodo are conveniently prepared by reacting corresponding compounds of formula IIc in which $L'''$ is chloro, with sodium iodide in acetone, the reaction being carried out in conventional manner.

The compounds of formula II in which L is alkylsulfonyloxy or arylsulfonyloxy, i.e. the compounds of formula IId

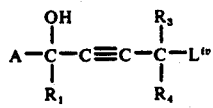   IId wherein
A, $R_1$, $R_3$ and $R_4$ are as defined above and
$L^{iv}$ is alkylsulfonyloxy or arylsulfonyloxy as defined above can be prepared by reacting a compound of the formula IX above with an appropriate alkylsulfonyl chloride, such as methanesulfonyl chloride, 3-chloropropanesulfonyl chloride or 1-hexadecanesulfonyl chloride or arylsulfonyl chloride, such as benzenesulfonyl chloride, 4-toluenesulfonyl chloride or 2-naphthalenesulfonyl chloride. This reaction is conveniently carried out in pyridine at or about room temperature.

The compounds of formula IIIa and IIIb used in the reduction of compounds II are known.

The compounds of formula IV used in the preparation of compounds Ib can be produced by isomerizing a compound of the formula X

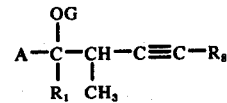   X wherein A, $R_1$, $R_8$ and G are as defined above with a strong base, e.g. sodium hydroxide or potassium hydroxide in a suitable solvent, such as ethanol, butanol, dimethyl acetamide or, preferably, dimethyl sulphoxide. The isomerization is carried out at a temperature of up to 160° C., preferably 50° C. to 90° C., and preferably in the absence of water.

The compounds of formula V above can be prepared by reacting a compound of formula VII above with a compound of formula XI

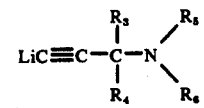   XI wherein $R_3$, $R_4$, $R_5$ and $R_6$ are as defined above. This reaction can be carried out at temperatures of 0° to 50° C., conveniently at room temperature, and in the presence of an organic solvent such as tetrahydrofuran.

The compounds of formula V can also be prepared by a process which involves reacting a compound of formula XII

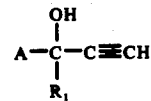   XII wherein A and $R_1$ are as defined above, with a product formed by condensing a compound of formula XIII

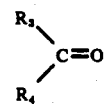   XIII wherein $R_3$ and $R_4$ are as defined above, with a compound of formula XIV

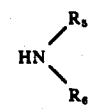   XIV wherein $R_5$ and $R_6$ are as defined above, said condensation product preferably prepared under conditions whereby water is eliminated when either of $R_3$ and $R_4$ is other than hydrogen.

The condensation of compounds XIII and XIV is preferably carried out separately at temperatures of from 10° to 130° C., and when either of $R_3$ and $R_4$ is alkyl, it is preferably carried out at the higher temperature, e.g. reflux in the presence of an acid catalyst such as paratoluene sulfonic acid and a solvent such as benzene which is capable of forming an azeotrope with the water formed. The condensation product is reacted with the compound of formula XII at a temperature of 50° to 150° C. in the presence of an inert solvent, and preferably in the presence of mono-valent copper ion, as catalyst, preferably cuprous chloride or cuprous oxide, although salts and the like of other coinage metals, i.e., silver and gold (I), can be used.

The compounds of formula VI above are known per se or can be prepared from known materials by conventional methods.

The compounds of formula VII used in the production of compounds IIb are known or can be prepared from known compounds using conventional techniques.

The compounds of formula VIII are prepared by reacting a propargyl alcohol with dihydrofuran, dihydropyran or 4-methoxy-5,6-dihydro-2H-pyran in the presence of hydrochloric acid, phosphorus oxychloride or other condensation agent.

The compounds of formula IX used in the production of compound IIc and IId can be prepared by conventional hydrolysis of a compound of formula IIb, such as with a mineral or organic acid.

The compounds of formula X above are prepared by reacting a compound of formula XV

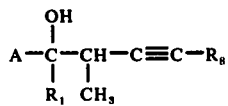

wherein A, $R_1$ and $R_8$ are as defined above, with dihydrofuran or dihydropyran in a manner similar to that described above for the preparation of compounds of formula VIII.

The compounds of formula XI are known or can be produced in known manner by reacting a compound of the formula XVI

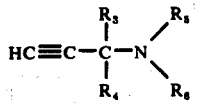

wherein $R_3$, $R_4$, $R_5$ and $R_6$ are as defined above with lithium at a temperature of 0° to 50° C. in a suitable solvent such as ethylene diamine. The compounds of formula XII can be prepared by reacting a compound of formula VII above in a solvent such as dimethyl acetamide or dimethyl sulfoxide with a suitable acetylene reagent, such as sodium or lithium acetylide conveniently at room temperature.

The compounds of formulae XIII and XIV used in the preparation of compound V are known or can be produced from known materials by conventional techniques.

The compounds of formula XV can be prepared by reacting a compound of formula VII with a suitable organo-metallo reagent XVII

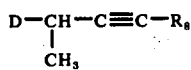

wherein
$R_8$ is as defined above, and
D is an equivalent unit of either an active metal or a polyvalent active metal halide, e.g., an alkali metal, such as lithium, potassium or sodium, aluminum, zinc, or magnesium bromide or iodide
to obtain the D salt of the resulting compound XV, which on hydrolysis yields the desired compound XV.

The procedure may be carried out under conditions conveniently employed in carrying out "Grignard-type" reactions, e.g., in an aprotic organic medium at a temperature of from about −30° to 100° C., preferably from about −20° to 50° C., followed by standard hydrolysis of the resulting D salt in an aqueous medium, e.g. water or a highly concentrated aqueous salt solution, e.g., saturated ammonium chloride solution. The medium used is dependent upon the composition of the organo-metallo reagent. For example, if D is MgBr, MgI or Li, the medium may be ether or tetrahydrofuran, if D is Na, the medium may be liquid ammonia-ether, liquid ammonia-tetrahydrofuran, dioxane, pyridine or dioxane-pyridine. The temperature and medium are not critical.

The compounds of formula XVI and XVII are known or can be produced in known manner from available materials.

Compounds Ib may also be obtained by an alternative process (process b') which involves treating a Compound VII with a Grignard reagent prepared from a compound of formula XX

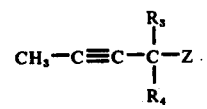

in which $R^3$ and $R^4$ are as defined above, and Z is bromo, chloro or iodo, and hydrolyzing the resulting product, i.e., the corresponding "Grignard salt" of the resultant Compound Ib.

In process b'), the reaction of the Grignard reagent with the compound of formula VII and the subsequent hydrolysis may be carried out in conventional manner. Preferred solvents for the reaction include diethyl ether, tetrahydrofuran, dioxane, benzene and toluene. Preferred temperatures for the reaction are from −10° to +90° C, more perferably from +25° to +65° C. It is preferred to exclude moisture from the reaction. The reaction is advantageously carried out under an inert atmosphere, e.g., of nitrogen or argon. The hydrolysis may conveniently be effected by careful addition to the reaction mixture of water, aqueous sodium sulphate solution, aqueous ammonium chloride solution or dilute acid. The Grignard reagent may be produced in the conventional manner. The resulting compound Ib likewise may be isolated in conventional manner.

The compounds of formula I are useful because they possess pharmacological activity in animals. In particular, the compounds I are useful as anti-inflammatory agents as indicated by the Carrageenan induced edema test on rats (oral administration at to 200 mg/kg). For such use, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 1 milligram to about 250 milligrams per kilogram, e.g., from about 1 milligram to about 175 milligrams per kilogram, of body weight, preferably given in divided doses 2 to 4 times a day, or in sustained release form. For most mammals, the administration of from about 20 milligrams to about 3000 milligrams, e.g., from about 80 milligrams to about 1000 milligrams, of the compound per day provides satisfactory results and dosage forms suitable for internal administration comprise from about 5 milligrams to about 1500 milligrams, e.g., from about 40 milligrams to about 500 milligrams, of the compound in admixture with a solid or liquid pharmaceutical carrier or diluent.

Those compounds of formula I in which Y is a unsubstituted or substituted phenyl group as above defined are also useful as sedative-hypnotics and tranquilizers as indicated in tests in mice (10 to 200 mg/kg), for example, by behavioral tests using a 30-word adjective check sheet, as described by Irwin (Gordon Research Conference, Medical Chemistry, 1959) and Chen (Symposium on Sedative and Hypnotic Drugs, Williams and Wilkins, 1954) and by their effect on N-sulfamoylazepine-evoked tonic convulsions and by their effect on hexobarbitol anesthesia when administered immediately after administration of hexobarbitol in a modification of the method reported by Winter (J. Pharmacol. and Exp. Therap., 94: 7, 1948). For such use, the compound may be administered in the same forms as mentioned above, with satisfactory results being obtained when administered at a daily dosage of from 2 milligrams to about 200 milligrams per kilogram of body weight. For most mammals the administration of from about 150 milligrams to about 2000 milligrams of the compound per day provides satisfactory results, with dosage forms suitable for internal administration comprising from about 40 to about 1000 milligrams of the compound in admixture with a solid or liquid pharmaceutical carrier or diluent.

For the above usage, oral administration with carriers may take place in such conventional forms as tablets, dispersible powders, granules, capsules, syrups and elixirs. Such compositions may be prepared according to any method known in the art for manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain the active ingredient admixed with an inert diluent, e.g., calcium carbonate, calcium phosphate, kaolin or polyethylene glycol. The preferred pharmaceutical compositions from the standpoint of preparation and ease of administration are solid compositions, particularly tablets and solid or liquid diluent-filled capsules.

When the substituent Y is a radical of structures $a^1$ or $a^2$ then such compounds I may be similarly administered in the form of their non-toxic pharmaceutically acceptable acid addition salts. Such salts do not materially differ from the free base in their pharmacological effects and are included within the scope of the invention. The acid addition salts are readily prepared by reacting the base with pharmacologically acceptable acids in conventional manner. Representative of such salts are the mineral acid salts such as the hydrochloride, hydrobromide, sulfate, phosphate and the like and the organic acid salts such as the benzoate, acetate, maleate, fumarate, p-toluenesulfonate, benzenesulfonate and the like.

A particularly valuable compound of this invention is 2-(p-biphenyl)-3,4-pentadien-2-ol.

The anti-inflammatory activity of certain Compounds I is also exhibited in the adjuvant arthritis test (oral administration 5 to 200 mg/kg) in rats using Mycobacterium butyricum in Freund's adjuvant, e.g., 2-(p-biphenylyl)-3,4-pentadien-2-ol.

Representative formulations for administration, 2 to 4 times a day, in treating inflammation are tablets and capsules prepared by conventional techniques and containing the following:

| Ingredient | Weight in Milligrams | | |
|---|---|---|---|
| | Tablet | Capsule | Capsule |
| 2-(p-biphenylyl)-3,4-pentadien-2-ol | 50 | 50 | 30 |
| Tragacanth | 10 | | |
| Lactose | 197.5 | 250 | |
| Corn Starch | 25 | | |
| Talcum | 15 | | |
| Magnesium Stearate | 2.5 | | |
| Polyethylene Glycol (M.W. 6000) | | | 300 |

In the following examples which are illustrative of the invention, temperatures are in degrees centragrade, and room temperature is 20° to 30° C., unless indicated otherwise.

EXAMPLE 1

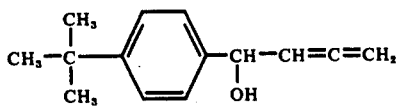

1-(p-tert-butylphenyl)-2,3-butadien-1-ol

STEP A

To a grignard mixture prepared as usual from 7.3 g of magnesium and 35.7 g of ethyl bromide in a total of 167 ml of dry tetrahydrofuran, there is dropwise added a solution of 40.6 g of 3-(2'-tetrahydropyranyloxy)-propyne in 40 ml of dry tetrahydrofuran. After 1 hour at room temperature a solution of 35.6 g of p-tert. butylbenzaldehyde in 71 ml of dry tetrahydrofuran is dropwise added. After 18 hours at 25°, 15 ml of aqueous 1 N sodium hydroxide solution is dropped in, followed by 20 g of anhydrous sodium sulfate. The filtered solution is evaporated to dryness, the residue taken up in benzene, washed with aqueous 1 N sodium hydroxide solution followed by water, dried and evaporated. On distillation at 150° bath temperature and at 0.3 mm pressure, the pure 1-(p-tert-butylphenyl)-4-(2'-tetrahydropyranyloxy)-2-butyn-1-ol is obtained as a colorless oil.

STEP B

To a solution containing 32 g of 1-(p-tert-butylphenyl)-2-(2'-tetrahydro-pyranyloxy)-2-butyl-1-ol, in 100 ml of anhydrous ether, there is added, portionwise, 4.8 g of lithium aluminum hydride. After 3 hours at room temperature, carefully, 4 ml of water is added followed by 10 g of sodium sulfate. The filterd solution is evaporated and the crude oily product filtered (silica gel G colunm, benzene-triethylamine 99:1 as eluent) to give 1-(p-tert-butylpheyl-2,3-butadien-1-ol as an oil.

When Example 1 is repeated using 3-(2'-tetrahydropyranyloxy)-3-methyl-1-butyne instead of 3-(2'-tetrahydropyranyloxy)-propyne, there is obtained 1-(p-tert-butylphenyl-4-methyl-2,3-pentadien-1-ol as an oil. With further substitution of p-bromoacetophenone for the p-tert-butyl benzaldehyde there is obtained 2-(p-bromophenyl)-5-methyl-3,4-hexadien-2-ol.

When Example 1 is repeated using p-phenylacetophenone and 1'-cyclohexenyl acetophenone in place of the p-tert butylbenzaldehyde, there is obtained 2-(p-biphenylyl)-3,4-pentadien-2-ol m.p. 65° to 66°, and 2-(p-1'-cyclohexenylphenyl)-3,4-pentadien-2-ol, respectively.

EXAMPLE 2

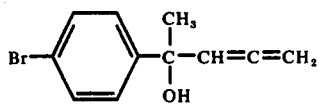

2-(p-Bromophenyl)-3,4-pentadien-2-ol

STEP A

In 500 ml of ethylene diamine there is dissolved 13.88 g of lithium wire. After the disappearance of the blue color, the grey suspension obtained is dropwise treated, at 5° C, with 166.3 g of 3-dimethylamino-1-propyne. After 1 hour at room temperature, a solution of 50 g of p-bromoacetophenone in 250 ml of tetrahydrofuran is added. After 2 hours at room temperature, the mixture is poured onto ice and extracted with chloroform to give 62.9 g of crude, 2-(p-bromophenyl)-5-dimethylamino-3-pentyn-2-ol which is dissolved in 500 ml of acetone and treated with 18 ml of methyl iodide. After 18 hours at 5°, the solution is evaporated to dryness and the residue triturated with chloroform-ether to give 68 g of pure 2-(p-bromophenyl)-5-dimethylamino-3-pentyn-2-ol methiodide, mp 185°–190°.

STEP B

To 500 ml of dry pyridine, there is added 500 mg of lithium aluminum hydride. Portionwise then, at 15°–20° there is added 25 g of the product of step a). After dissolution, 2.5 g more of lithium aluminum hydride is portionwise added. After 2 hours, 3 ml of 15% aqueous sodium hydroxide solution is dropwise added, followed by 5 ml of water and the slurry is filtered through a layer of Celite. The pyridine is stripped off at 40°, the oily residue re-dissolved is benzene, the benzene solution is washed with water, dried over sodium sulfate and evaporated. Crystallization from ether and vacuum distillation yields 2-(p-bromophenyl)-3,4-pentadien-2-ol, mp 45°–50° C.

When Example 2 is repeated using p-isobutyl acetophenone in place of p-bromoacetophenone there is obtained 2-(p-isobutylphenyl)-3,4pentadien-2-ol.

EXAMPLE 3

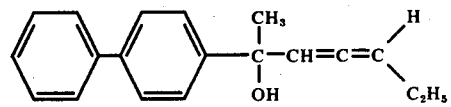

2-(p-Biphenylyl)-3,4-heptadien-2-ol

STEP A

To a solution of 46.6 g of p-phenylacetophenone in 250 ml. of dimethyl sulfoxide, there is added 65.5 g of lithium acetylide - ethylene diamine complex. After 18 hours at room temperature, the mixture is poured on 2 liters of iced water. The initial oil solidifies on standing, is filtered off and recrystallized from 150 ml of isopropyl alcohol to give 2-(p-biphenylyl)-3-butyn-2-ol, mp 75°–80° C.

STEP B

An intimate mixture of 29.94 g of 2-(p-biphenylyl)-3-butyn-2 -ol, 17.58 g of 1-(1'-piperidyl)-1-propene and of 17.27 g of cuprous chloride is kept at 60° C for 1 hour. After cooling, the mixture is stirred with 300 ml of ether and the filtered ether solution is washed 5 times with ice cold water. After drying over $NaSO_4$, the filtered ethereal solution is evaporated to dryness to yield the crude 2-(p-biphenylyl)-5-(1'-piperidyl)-3-heptyn-2-ol as a solid.

STEP C 25 g of the 2-(p-biphenylyl)-5-(1'-piperidyl)-3-heptyn-2-ol, dissolved in 125 ml of acetonitrile, is treated with 18 g of methyl iodide. After 18 hours at 5° C, the mixture is evaporated to dryness and the residue is triturated with dry ether whereupon crystalline 2-(p-biphenylyl)-5-piperidyl)-3-heptyn-2-ol methiodide, is obtained.

STEP D

The product of step c is reacted with lithium aluminum hydride analogously to Example 2, step b to produce 2-(p-biphenylyl)-3,4-heptadien-2-ol. b.p. 165°–175° at, 88 mm.

EXAMPLE 4

Following the procedure of Examples 1, 2 or 3 and using appropriate starting materials in approximately equivalent amounts, there is obtained;

a. 2-(p-isobutylphenyl)-5-methyl-3,4-hexadien-2-ol, as a liquid.

b. 2-[p-(4'-methoxyphenyl)-phenyl]-3,4-pentadien-2-ol, m.p. 77°–82°, c. 1-(p-biphenylyl)-2,3-butadien-1-ol, as a liquid, d. 2-(p-biphenylyl)-5-methyl-3,4-hexadien-2-ol, b.p. 135° at 0.15 mm, e. 2-[p-(4'-chlorophenyl)-phenyl]-3,4-pentadien-2-ol, m.p. 106°, f. 3-(p-biphenylyl)-4,5-hexadien-3-ol, b.p. 150°–160° at 0.075 mm, g. 2-[p-(4'-fluorophenyl)-phenyl]-3,4-pentadien-2-ol, m.p. 70°–81° C, h. 2-(p-cyclohexylphenyl)-3,4-pentadien-2-ol, m.p. 157°–162°, i. 2-[p-(1-methyl-4-piperazinyl)-phenyl(]-3,4-pentadien-2-ol in fumarate salt form, m.p. 128°–131°, and j. 2-(p-morpholino-phenyl)-3,4-pentadien-2-ol, m.p. 76°–82°.

k. 2-(p-cyclohexyl-m-chlorophenyl)-3,4-pentadien-2-ol.

EXAMPLE 5

2-(p-Biphenylyl)-3-methyl-3,4-pentadien-2-ol*

* may also be designated 4-(p-biphenylyl)-3-methyl-1,2-pentadien-4-ol

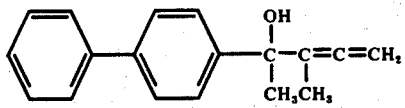

To a Grignard reagent prepared in the usual manner from 6.8 g of 1-bromo-2-butyne and 2.0 g of magnesium in 150 ml of dry tetrahydrofuran, there is added, dropwise, a solution of 10 g of 4-acetylbiphenyl** dissolved in 50 ml of dry tetrahydrofuran. After addition, the reaction mixture is refluxed for 40 minutes. The reaction mixture is then allowed to cool to room temperature and, after standing at room temperature for 18 hours, the reaction mixture is poured into a cold dilute aqueous solution of ammonium chloride. The mixture is extracted several times with chloroform, the extractions being collected, washed with water, dried over anhydrous magnesium sulphate, filtered and evaporated to dryness. The crude product is subjected to preparative chromatography, using silica gel plates and 1% triethylamine/chloroform solvent system to obtain 2-(p-biphenylyl)-3-methyl-3,4-pentadien-2-ol.

** may also be designated p-phenyl-acetophenone

EXAMPLE 6

2-(p-biphenylyl)-3,4-pentadien-2-ol

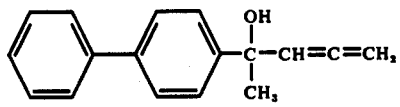

STEP A 2-(p-biphenylyl)-5-dimethylamino-3-pentyn-2-ol

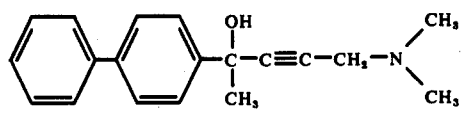

In a nitrogen gas atmosphere, there is charged to a reaction vessel 8.5 liters of ethylene diamine (freshly distilled from potassium hydroxide), and heated to 40° C. Over a period of 2 hours, 243 g of lithium wire (34.8 moles) is gradually added with agitation while the temperature is raised to 110° C. The reaction mixture turns blue. The mixture is maintained with stirring at 100° to 110° for 2 additional hours. The mixture turns yellow brown. The mixture is cooled to 15° C, and with stirring and cooling (20° to 28°), 2890 g of 3-dimethylamino-1-propyne (34.8 moles) is added dropwise over a period of 2 hours. The reaction mixture becomes very thick (brown), and is stirred for an additional hour at room temperature. 850 g of p-phenylacetophenone in 8.5 liters of tetrahydrofuran is added to the reaction mixture in one portion at room temperature and the mixture stirred for 2 hours at room temperature. The mixture is then poured into 50 liters of ice water and the resulting mixture maintained at 0° to 10°. A gummy precipitate forms, and is recovered by filtration, and washed with cold water. The filter cake is dissolved in 10 liters of methylene chloride, water separated, and the methylene chloride solution dried over sodium sulfate, and solvent removed by rotary evaporation, to obtain a red oil, which is further dried under high vacuum to give a foam (containing 2-(p-biphenyl)-5-dimethylamino-3-pentyn-2-ol and about 60% of p-phenylacetophenone).

STEP B methiodide of 2-(p-biphenylyl)-5-dimethylamino-3-pentyn-2-ol 1479 g of the 2-(p-biphenylyl)-5-dimethylamino-3-pentyn-2-ol containing product, obtained by carrying out step a) above, is dissolved in a mixture of 5 liters acetone and 1 liter of methylene chloride. The solution is cooled to 5° and with vigorous stirring, over a period of 1 hour at 0° to 5°, 876 g of methyl iodide is gradually added. Stirring is continued for 12 hours at 5° to 10°. Solvents are removed by rotary evaporation at 30° to obtain a thick residue, which is then poured into 20 liters of diethyl ether with vigorous stirring. A precipitate forms which is collected by filtration. The filter cake is washed four times with diethyl ether. The filter cake is then dried under high vacuum for 12 hours at room temperature to obtain the methiodide of 2-(p-biphenylyl)-5-dimethylamino-3-pentyn-2-ol as a crude foam, (m.p. 60° to 84°).

STEP C 2-(p-biphenylyl)-3,4-pentadien-2-ol

To a suspension of 507 g of the crude (foam) methiodide of 2-(p-biphenylyl)-5-dimethylamino-3-pentyn-2-ol obtained by step b) above, in 4 liters of dry tetrahydrofuran, is added dropwise over a period of one hour, with cooling (to keep at room temperature), 478 g of a solution of sodium dihydrobis (2-methoxyethoxy) aluminate 70% w/w in benzene in 800 ml of dry tetrahydrofuran. The resulting mixture is then stirred at room temperature for 2 hours. The mixture is then cooled to 10° and dropwise there is added 3 liters of 2N sodium hydroxide, with stirring and cooling to 10° to 20°. 10 liters of diethyl ether are then added, in one portion, to the mixture. Solids present (inorganic salts) are removed by filtration on Celite. The filtrate is then extracted twice with 5 liter portions of water, the water washes then being washed three times with 5 liters of diethyl ether each time. The combined ether phases are washed once with 3 liters of aqueous saturated brine solution. The combined organic phases are dried over sodium sulfate, filtered, and the filtrate evaporated by rotary evaporation at 40° to obtain the crude product as an oil. The oil is taken up in 7 liters pentane (heated) and then the resulting pentane solution chilled until a precipitate forms. The precipitate is collected by filtration and washed with pentane. The precipitate is crystallized from pentane five times, then dried in a vacuum oven at room temperature for 12 hours to yield the title product, m.p. 65°–66°.

Following the procedure of this example, but using in place of the p-phenylacetophenone, an approximately equivalent amount of
a. p-(p-methoxyphenyl)-acetophenone, or
b. p-(p-fluorophenyl)-acetophenone,
there is similarly obtained
a. 2-[p-(4'-methoxyphenyl)-phenyl]-3,4-pentadien-2-ol, or
b. 2-[p-4'-fluorophenyl)-phenyl]-3,4-pentadien-2-ol.

What is claimed is:

1. A compound of the formula

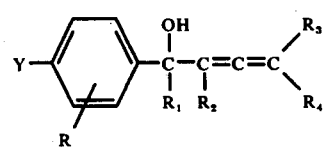

wherein
R is a hydrogen atom, or halo having an atomic weight of from about 19 to 80;
$R_1$ is a hydrogen atom or alkyl of 1 to 3 carbon atoms;
$R_2$ is a hydrogen atom or methyl; and
$R_3$ and $R_4$ are, independently, a hydrogen atom or alkyl of 1 to 3 carbon atoms, provided that at least one of $R_3$ and $R_4$ is a hydrogen atom when $R_2$ is methyl;
Y is bromo, iodo, isobutyl, tert. butyl, cyclohexyl, or cyclohexenyl.

2. A compound of claim 1 wherein $R_2$ is a hydrogen atom.

3. A compound of claim 2 in which both $R_3$ and $R_4$ are hydrogen atoms.

4. The compound of claim 3 which is 1-(p-tert.-butylphenyl)-2,3butadien-1-ol.

5. The compound of claim 3 which is 2-(p-1'-cyclohexylphenyl)-3,4-pentadien-2-ol.

6. The compound of claim 3 which is 2-(p-bromophenyl)-3,4-pentadien-2-ol.

7. The compound of claim 3 which is 2-(p-isobutylphenyl)-3,4-pentadien-2-ol.

8. The compound of claim 3 which is 2-(p-cyclohexyl-m-chlorophenyl)-3,4-pentadien-2-ol.

9. The compound of claim 3 which is 2-(p-cyclohexylphenyl)-3,4-pentadien-2-ol.

10. The compound of claim 2 in which both $R_3$ and $R_4$ are methyl.

11. The compound of claim 10 which is 1-(p-tert.-butylphenyl)-4-methyl-2,3-pentadien-1-ol.

12. The compound of claim 10 which is 2-(p-bromophenyl)-5-methyl-3,4-hexadien-2-ol.

13. The compound of claim 10 which is 2-(p-isobutylphenyl)-5-methyl-3,4-hexadien-2-ol.

14. The compound of claim 1 in which $R_2$ is methyl.

15. A compound of claim 1 in which $R_1$ is alkyl.

16. A compound of claim 15 in which $R_2$ is hydrogen.

17. A compound of claim 16 in which $R_3$ and $R_4$ are hydrogen.

18. The method of treating inflammation in an mammal which comprises administering to said mammal an inflammation relieving amount of a compound of claim 1.

19. A pharmaceutical composition useful for the treatment of inflammation in mammals comprising an inflammation relieving amount of a compound of claim 1 and a pharmaceutically acceptable carrier.

* * * * *